(12) United States Patent
Stichter et al.

(10) Patent No.: US 7,151,192 B2
(45) Date of Patent: Dec. 19, 2006

(54) MANUFACTURING PROCESS FOR THE PREPARATION OF α,α-BRANCHED ALKANE CARBOXYLIC ACIDS PROVIDING ESTERS WITH AN IMPROVED SOFTNESS

(75) Inventors: Hendrik Stichter, Amsterdam (NL); Leonardus Petrus, Amsterdam (NL); Hans Arie Stil, Amsterdam (NL)

(73) Assignee: Hexion Specialty Chemicals, Inc., Columbus, OH (US)

( * ) Notice: Subject to any disclaimer, the term of this patent is extended or adjusted under 35 U.S.C. 154(b) by 327 days.

(21) Appl. No.: 10/484,129

(22) PCT Filed: Jul. 2, 2002

(86) PCT No.: PCT/EP02/07538

§ 371 (c)(1), (2), (4) Date: Jan. 16, 2004

(87) PCT Pub. No.: WO03/011806

PCT Pub. Date: Feb. 13, 2003

(65) Prior Publication Data

US 2005/0176979 A1 Aug. 11, 2005

(30) Foreign Application Priority Data

Jul. 31, 2001 (EP) ................................. 01202901

(51) Int. Cl.
*C07C 51/00* (2006.01)
(52) U.S. Cl. ........................ 562/497; 560/232; 549/513
(58) Field of Classification Search ................. 560/232; 562/497; 549/513
See application file for complete search history.

(56) References Cited

U.S. PATENT DOCUMENTS

| 2,967,873 | A | | 1/1961 | Koch et al. |
| 5,229,461 | A | * | 7/1993 | Saitoh et al. ................ 525/200 |
| 5,430,179 | A | * | 7/1995 | Lincoln et al. .............. 560/261 |
| 6,211,406 | B1 | | 4/2001 | Lange et al. |
| 6,281,372 | B1 | | 8/2001 | Wiese et al. |
| 6,433,242 | B1 | | 8/2002 | Wiese |

FOREIGN PATENT DOCUMENTS

DE 972291 7/1959

OTHER PUBLICATIONS

Toho Chemical Industry Co., Ltd., 1983, CAS: 98: 139012.*

* cited by examiner

*Primary Examiner*—Joseph K. McKane
*Assistant Examiner*—Robert Shiao
(74) *Attorney, Agent, or Firm*—Lisa Kimes Jones

(57) ABSTRACT

A manufacturing process for the preparation of α,α-branched alkane carboxylic acids, by reacting a mono-olefin or a precursor thereof, with carbon monoxide in the presence of a strong acid catalyst characterized in that the starting olefin is a dimmer C8 or trimer C12 derived from n-butene, which predominantly comprise 2-butene, that the acid catalyst is composed of $BF_3/H_3PO_4$ in a molar ratio of $BF_3:H_3PO_4$ in the range of from 0.5:1.0 to 5.0:1.0, or of $CF_3SO_3H$, that the weight ratio of the catalyst relative to the mono-olefin is in the range of from 1:1 to 10:1, that the reaction is carried out at a temperature in the range of from 60 to 140° C., and with an initial water content in the catalyst system in the range of from 8 to 25 wt %; and vinyl esters and glycidyl esters derived from said carboxylic acids.

10 Claims, No Drawings

MANUFACTURING PROCESS FOR THE PREPARATION OF α,α-BRANCHED ALKANE CARBOXYLIC ACIDS PROVIDING ESTERS WITH AN IMPROVED SOFTNESS

The present invention relates to a manufacturing process for the preparation of α,α-branched alkane carboxylic acids providing esters with an improved softness.

More in particular the invention relates to the preparation of aliphatic tertiary saturated carboxylic acids or α,α-branched alkane carboxylic acids, which contain 9 or 13 carbon atoms and which provide esters with an improved softness.

It is generally known from e.g. U.S. Pat. Nos. 2,831,877, 2,876,241, 3,053,869, 2,967,873 and 3,061,621 that mixtures of α,α-branched alkane carboxylic acids can be produced, starting from mono-olefins, carbon monoxide and water, in the presence of a strong acid.

As mono-olefins starting materials, dimers and trimers of isobutylene were inter alia used.

From e.g. H van Hoorn and G C Vegter, Dynamic modulus measurements as a tool in the development of paint base materials FATIPEC, Euro Continental Congress 9, Pleniere p. 51–60 (1968); Rheol. Acta 10, p. 208–212 (1971); H van Hoorn, the influence of side group structure on the glass transition temperature of isomeric vinyl ester polymers, the relation between the final coating film properties and the isomer distribution in starting branched carboxylic acids, was known.

In such mixtures of α,α-branched alkane carboxylic acids, significant proportions of blocking β-methyl-branched carboxylic acid isomers were found, the properties of which have been found to antagonize the attractive properties of other α,α-branched saturated carboxylic acid constituents of said mixtures, when applied in the form of derivatives such as glycidyl esters or vinyl esters in the coating industry, requiring more and more so-called softer acid derivatives.

More in particular the conventionally produced α,α-branched carboxylic acid mixtures had been found to cause a too high hardness of the final coating of films, which was disadvantageous and therefore undesired for certain applications, due to the presence of significant proportions of blocking β-alkyl-branched isomers.

One of the more recent remedies has been disclosed in EP 1033360A1. The problem of providing better softening derivatives of α,α-branched acids, manufactured from alkenes, carbon monoxide and water and an acid catalyst was solved therein by a process, which actually comprised:
(a) oligomerisation of n-butene, comprising predominantly 2-butene;
(b) separation of butene dimers and/or trimers from the oligomerisate;
(c) conversion of the butene dimers and/or trimers into carboxylic acids;
(d) conversion of the carboxylic acids into the corresponding vinyl esters showing attractive softening properties when mixed into other polymers or if used as comonomers in coatings.

These attractive properties were shown only to be reached by application of a specifically selected "OCTOL" oligomerisation process, as known from e.g. Hydrocarbon Processes Int. Ed. (1986), 65 (2, sect. 1), pages 31–33, whereas said attractive properties of the final vinyl esters could not be reached by prior art alternatives, i.e. oligomerisation processes using acid Montmorillonite catalyst or a DIMERSOL process, known from e.g. Cornils, Hermann, Applied Homogeneous Catalysis with Organomettalic Compounds, p 261–263, Verlag Chemie 1996. Said OCTOL process uses a so called Raffinate III fraction, which was rich of 2-butene, and the obtained specific dimers or trimers were subsequently converted into carboxylic acids by means of a process using as catalyst a strong acid such as sulfonic acids or a complex of boron fluoride and water and $Cu^+$ ions as co-catalyst and temperatures in the range of from 20 to 35° C. and a CO pressure of at least 30 bar.

With the term "predominantly comprising 2-butene" as used throughout the present specification is meant that the starting n-butene feed comprises at least 70 wt % of 2-butene and preferably at least 85 wt %.

More in particular, it was known from said EP 1033360A1 that vinyl esters with significantly improved softening properties could be reached depending on the branching degree in the starting olefin, to be used for the manufacture of α,α-branched carboxylic acids.

This disclosure taught that the Tg of the homopolymer of vinyl esters of carboxylic acids derived from a n-butene feed predominantly comprising 2-butene feed, by acid catalysed (Montmorillonite) oligomerisation of butene is +38° C. and is therefore a "hard" comonomer. The Tg of the homopolymer of the vinyl ester of carboxylic acids derived from a dibutene obtained by the DIMERSOL oligomerisation process of a n-butene, predominantly comprising 2-butene, is considerably lower, i.e. +1° C.

The object of the process of EP 1 033 360 A1 were branched carboxylic acids, which were prepared from butene dimers, obtainable by the OCTOL oligomerisation process from a n-butene starting material, predominantly comprising 2-butene and containing not more than 35 wt % of multi-branched olefins, such as dimethylhexene, and preferably at most 25 wt %.

Moreover said carboxylic acids, having a significantly increased content of 2,2-dimethyl heptanoic acid and 2-ethyl,2-methyl hexanoic acid, and a decreased content of 2,3-dimethyl-2-ethyl pentanoic acid, could provide the presently required attractive properties of the corresponding vinyl esters, such as a Tg of –3° C. at the lowest for the homopolymer of said $C_9$ vinyl ester.

Another object of the disclosed process in said EP 1 033 360 A1 were branched $C_{13}$ carboxylic acids, which were prepared from butene trimers obtainable by the OCTOL oligomerisation process. Moreover said carboxylic acids, could only provide the presently required attractive properties of the corresponding vinyl esters, such as a Tg of –13° C. at the lowest for the homopolymer of said $C_{13}$ vinyl ester.

A further improved embodiment could be reached by application of a process disclosed in EP 1 029 839 A disclosing a process for fractionation of the dibutene mixtures from the OCTOL process, i.e. mixtures of $C_8$ olefins, in order to obtain branched carboxylic acids of which the homopolymer of the corresponding vinyl $C_9$ esters show a still lower Tg, i.e. –12° C.

In said publication there is not any teaching to a skilled person as to the effects of fractionation of tributene oligomers, in order to reach softer branched $C_{13}$ alkane carboxylic acids.

It will be appreciated that said disclosures taught to a person skilled in the art that vinyl esters of α,α-branched $C_9$ alkane carboxylic acids, having homopolymers with a Tg as low as –12° C., could only be obtained by a process comprising oligomerisation of n-butene predominantly comprising 2-butene, by means of the OCTOL process, followed by distillative fractionation of the oligomer mixture, conversion of the bottom fraction into α,α-branched alkane carboxylic acids, and subsequently conversion to the corresponding vinyl ester, which will increase the cost price per unit as compared with conventional processes.

It will be appreciated that there is a still growing need for aliphatic tertiary saturated carboxylic acids, which gives rise to softer coating films, formed from their derivatives, such as glycidyl esters or vinyl esters, and which will be further referred to as "soft α,α-branched alkane carboxylic acids" and which can be simultaneously be manufactured without additional fractionation of the olefin feed and therefore at lower manufacturing costs.

An object of the present invention is to provide such soft α,α-branched alkane carboxylic acids in order to attain more attractive properties of coatings derived therefrom.

With the term "soft α,α-branched alkane carboxylic acids", as used throughout the specification, are meant those acids of which the homopolymer of the corresponding vinyl esters show a Tg of −3° C. or lower in the case of $C_9$ acids and a Tg of −13° C. or lower in the case of $C_{13}$ acids.

As a result of extensive research and experimentation a process giving the branched carboxylic acids aimed at, has surprisingly been found.

Accordingly, the invention relates to a manufacturing process for the preparation of α,α-branched alkane carboxylic acids, the vinyl esters of which can provide homopolymers with a Tg of −3° C. or lower in case of $C_9$ acids and a Tg of −13° C. or lower in case of $C_{13}$ acids, by reacting a mono-olefin or a precursor thereof, with carbon monoxide in the presence of a strong acid catalyst characterized in that the starting olefin is a dimer or trimer derived from n-butene, comprising predominantly 2-butene, that the acid catalyst is composed of $BF_3/H_3PO_4$ in a molar ratio of $BF_3:H_3PO_4$ in the range of from 0.5:1.0 to 5.0:1.0, or of $CF_3SO_3H$, that the weight ratio of the catalyst relative to the mono-olefin is in the range of from 1:1 to 10:1, that the reaction is carried out at a temperature in the range of from 60 to 140° C., and with an initial water content in the catalyst system in the range of from 8 to 25 wt %.

According to a more preferred embodiment, using a $BF_3/H_3PO_4$ catalyst, the molar ratio between $BF_3$ and $H_3PO_4$ is in the range of from 1:1 to 3:1 and the carbon monoxide pressure is in the range of from 20 to 100 bar.

Preferably the reaction temperature is in the range of from 80 to 140° C. and the carbon monoxide pressure is in the range of from 30 to 90 bar. The preferred initial water content in the catalyst system is in the range from 8 to 25 wt %. More preferably the preferred initial water content is in the range of from 12 to 25 wt %.

Preferably the weight ratio of the catalyst relative to the mono-olefin is in the range of from 2:1 to 6:1.

The starting mono-olefin is a mixture of oligomers of butene.

It will be appreciated that the starting mono-olefins actually consist of several olefin isomers in varying proportions.

It will also be appreciated that the water content of the reaction mixture changes throughout the reaction since 1 mole of water is reacted on every mole of mono-olefin fed.

Usual reaction times of the present process are within the range of from 15 to 120 minutes. Preferred reaction times are within the range of from 20 to 90 minutes. More preferred reaction times are within the range of from 30 to 60 minutes.

It will be appreciated that the process of the present invention can be carried out as batch process, semi-batch and preferably as continuous process and that the starting olefins can be formed in situ from precursors.

Precursors for olefins which can be suitably used are e.g. alcohols, esters, or carboxylic acids. It will be appreciated that in case of application of e.g. an alcohol precursor for an olefin, the co-produced water forms a part of the total water amount as specified hereinbefore.

It will also be appreciated that the continuous process can be carried out as described by e.g. U.S. Pat. No. 3,068,256 and in "New Syntheses with Carbon Monoxide" J. Falbe, New York 1980, pages 406–408 and references cited therein.

The acid mixtures initially obtained can be purified by methods known per se, such as distillation.

It will be appreciated that the "softer" α,α-branched saturated carboxylic acids can be converted by known methods in their derivatives such as salts, esters, acid halides and more in particular glycidyl esters or vinyl esters, which can be used as attractive starting materials in the coating industry.

It has been surprisingly found that mixtures of α,α-branched alkane carboxylic acids, comprising higher proportions of soft isomers, could be prepared in a reproducible, preferably continuous way and starting from relatively cheap feedstock, preferably butene dimers or trimers derived from n-butene, predominantly comprising 2-butene.

It will be appreciated that, according to the process of the present invention, α,α-branched alkane carboxylic acids can be prepared of which the homopolymers of the corresponding vinyl esters have a Tg lower than −3° C. in the case of $C_9$ acids and lower than −13° C. in the case of $C_{13}$ acids, and said α,α-branched alkane carboxylic acids can be obtained from butene dimer $C_8$ or butene trimer $C_{12}$ olefins, using the "DIMERSOL" process or the "Montmorillonite catalyst" (OCTOL) process as oligomerisation process and without further fractionation of the butene dimer or butene trimer olefin feed, which will be regarded as very surprising to people skilled in the art.

Another aspect of the present invention is formed by the α,α-branched alkane carboxylic acids, obtainable by the hereinbefore defined process.

Still another aspect of the present invention is formed by esters, such as vinyl or glycidyl esters of said carboxylic acids e.g. by conversion of them with acetylene, e.g. as known from WO 98/16494, EP0512656B1 or EP0729448B1, or with epichlorohydrin, e.g. as known from WO/OO/17179 (PCT/EP99/07393), in the presence of a suitable catalyst.

The invention is further illustrated by the following examples, however without restricting its scope to these embodiments.

EXAMPLES

Example 1

A 250 ml Hastelloy C autoclave is continuously fed with 5.8 g/minute of a catalyst system, which consists of $BF_3/H_3PO_4$/water in a $BF_3/H_3PO_4$ molar ratio 1.5/1 and 1.1 g/minute butene trimer ($BT_3$) obtained by the DIMERSOL type process. The water content of the catalyst system is set to 13.0 wt %.

The autoclave is equipped with a manometer, a mechanically driven stirrer, a heating mantel, inlets for CO, olefins, fresh catalyst (for start-up), catalyst recycle stream, and a dip-tube for the continuous withdrawing of the product/catalyst mixture. The water recycle is returned to the reaction mixture just before the settling vessel.

The temperature in the autoclave is 112° C. and the carbon monoxide pressure of 80 bar is regulated via a back-pressure.

Subsequently the reaction mixture is separated in a settling vessel. The lower catalyst rich layer is recycled to the reactor and the upper organic layer is continuously washed, in a packed column, in counter current with water. The water layer from the washing column is recycled to the reactor outlet and the fresh water flow to the column is set a such a rate that the water concentration in the settling vessel maintains at a constant level. The organic layer contains the crude carboxylic acid mixture. The organic layer contains the crude carboxylic acid mixture in a yield of 89 wt % as determined by Gas Chromatography.

After removal of the light ends and heavy ends from the organic layer by distillation, the "soft" α,α-branched $C_{13}$ alkane carboxylic acid mixture is obtained.

Example 2

The mixture of α,α-branched alkane carboxylic acids as obtained from Example 1 is converted with acetylene at atmospheric pressure in the presence of the zinc salt of the starting α,α-branched alkane carboxylic acid mixture according to the method as described in e.g. WO98/16494. The Tg of the homopolymer of thus obtained vinyl ester was measured to be −32° C.

For comparison, the Tg of the homopolymer of the $C_{13}$ vinyl ester of the α,α-branched saturated carboxylic acid mixture as obtained by example 15 of EP 1033360 A1 of Oxeno Olefinchemie GmbH was determined to be −13° C.).

Example 3

A 250 ml Hastelloy C autoclave is continuously fed with 3.7 g/minute of a catalyst system, which consists of $BF_3$/$H_3PO_4$/water in a $BF_3$/$H_3PO_4$ molar ratio 1.5/1 and 0.54 g/minute butene dimer, obtained by the "DIMERSOL" type process ($BD_2$), 32% 3,4-dimethylhexene, 58.8% 3-methylheptene, 7.2% n-octene, 2% others. The water content of the catalyst system is set to 16.3 wt %.

The autoclave is equipped with a manometer, a mechanically driven stirrer, a heating mantel, inlets for CO, olefins, fresh catalyst (for start-up), catalyst recycle stream, and a dip-tube for the continuous withdrawing of the product/catalyst mixture. The water recycle is returned to the reaction mixture just before the settling vessel.

The temperature in the autoclave is 112° C. and the carbon monoxide pressure of 80 bar is regulated via a back-pressure.

Subsequently the reaction mixture is separated in a settling vessel. The lower catalyst rich layer is recycled to the reactor and the upper organic layer is continuously washed, in a packed column, in counter current with water. The water layer from the washing column is recycled to the reactor outlet and the fresh water flow to the column is set a such a rate that the water concentration in the settling vessel maintains at a constant level. The organic layer contains the crude carboxylic acid mixture in a yield of 87 wt % as determined by Gas Chromatography.

After removal of the light ends and heavy ends from the organic layer by distillation, the "soft" α,α-branched $C_9$ alkane carboxylic acid mixture is obtained.

Example 4

The mixture of α,α-branched alkane carboxylic acids as obtained from Example 3 is converted with acetylene at atmospheric pressure in the presence of the zinc salt of the starting α,α-branched alkane carboxylic acid mixture according to the method as described in e.g. WO98/16494. The Tg of the homopolymer of thus obtained vinyl ester was measured to be −8° C.

For comparison, the Tg of the homopolymer of the $C_9$ vinyl ester of the α,α-branched saturated carboxylic acid mixture as obtained by example 14 of EP 1033360 A1 of Oxeno Olefinchemie GmbH was determined to be −3° C.).

The invention claimed is:

1. A manufacturing process for the preparation of α,α-branched alkane carboxylic acids, the process comprising reacting a mono-olefin feed comprising a dimer ($C_8$) or trimer ($C_{12}$) of n-butene, comprising predominantly 2-butene, with carbon monoxide in the presence of a strong acid catalyst, wherein the n-butene dimer or n-butene trimer olefin feed has not been fractionated, wherein the acid catalyst is composed of $BF_3$/$H_3PO_4$ in a molar ratio of BF3:$H_3PO_4$ in the range of from 0.5:1.0 to 5.0:1.0, or of $CF_3SO_3H$, wherein a weight ratio of the catalyst relative to the mono-oletin is in the range of from 1:1 to 10:1, wherein the reaction is carried out at a temperature in the range of from 60 to 140° C. and wherein the catalyst has an initial water content in the range of from 8 to 25 wt %.

2. The manufacturing process of claim 1, wherein the catalyst is BF3/H3PO4 and wherein the molar ratio of $BF_3$:$H_3PO_4$ is in the range of from 1:1 to 3:1.

3. The manufacturing process of claim 1 wherein the carbon monoxide is at a pressure in the range of from 20 to 100 bar.

4. The manufacturing process of claim 1 wherein the reaction temperature is in the range of from 80 to 140° C. and the carbon monoxide is at a pressure is in the range of from 30 to 90 bar.

5. The manufacturing process of claim 1 wherein the weight ratio of the catalyst relative to the mono-olefin is in the range of from 2:1 to 6:1.

6. The manufacturing process of claim 1 wherein the manufacturing process is a continuous process.

7. The manufacturing process of claim 1 wherein the manufacturing process is a nickel catalyzed oligomerization process or an acid catalyzed oligomerization process.

8. The manufacturing process according to claim 7, wherein the manufacturing process is the acid catalyzed oligomerization process.

9. The process of claim 1 further comprising preparing glycidyl esters from the α,α-branched saturated carboxylic acids obtained according to the process of claim 1.

10. The process of claim 1 further comprising preparing vinyl esters from the α,α-branched saturated carboxylic acids obtained according to the process of claim 1, of which a homopolymer has a Tg lower than −3° C. in the case of $C_9$ acids and lower than −13° C. in the case of $C_{13}$ acids.

* * * * *